United States Patent
Gürtler et al.

(10) Patent No.: US 7,132,564 B2
(45) Date of Patent: Nov. 7, 2006

(54) PROCESS FOR PREPARING CYCLIC KETONES

(75) Inventors: Christoph Gürtler, Köln (DE); Jörg Kirchhoff, Köln (DE); Ido Schwarz, Düsseldorf (DE)

(73) Assignee: Bayer Materialscience AG, Leverkusen (DE)

( * ) Notice: Subject to any disclaimer, the term of this patent is extended or adjusted under 35 U.S.C. 154(b) by 0 days.

(21) Appl. No.: 11/243,174

(22) Filed: Oct. 4, 2005

(65) Prior Publication Data

US 2006/0079709 A1  Apr. 13, 2006

(30) Foreign Application Priority Data

Oct. 7, 2004  (DE) .................... 10 2004 048 875

(51) Int. Cl.
*C07C 69/74* (2006.01)
(52) U.S. Cl. ....................... 560/122; 560/126
(58) Field of Classification Search .................... None
See application file for complete search history.

(56) References Cited

U.S. PATENT DOCUMENTS

| 4,889,431 A | 12/1989 | Liechti ................... 366/99 |
| 4,950,081 A | 8/1990 | List, deceased ............... 366/85 |
| 5,334,358 A | 8/1994 | Schuchardt et al. ......... 422/210 |
| 5,407,266 A | 4/1995 | Dötsch et al. ................ 366/97 |
| 5,634,715 A | 6/1997 | Stehr et al. .................. 366/137 |
| 6,875,756 B1 | 4/2005 | Michels et al. ............... 514/57 |

FOREIGN PATENT DOCUMENTS

| DE | 85 560 | 11/1971 |
| DE | 2 055 009 | 5/1972 |
| DE | 100 54 854 A1 | 8/2001 |
| DE | 197 47 218 B4 | 7/2004 |
| EP | 611 937 B1 | 10/1998 |
| HU | 173 512 | 5/1979 |
| JP | 9-183755 | 7/1997 |

OTHER PUBLICATIONS

Toda et al, Journal of the Chemical Society, Perkin Trans. Jan. 1998, pp. 3521-3522.*

* cited by examiner

*Primary Examiner*—Paul A. Zucker
(74) *Attorney, Agent, or Firm*—Joseph C. Gil

(57) ABSTRACT

The present invention provides a process for preparing cyclic 1,3-keto esters in the absence of solvent, using solid-state or high viscosity reactors.

7 Claims, No Drawings

PROCESS FOR PREPARING CYCLIC KETONES

CROSS-REFERENCE TO RELATED APPLICATION

This application claims priority to German application DE 10 2004 048875, filed Oct. 7, 2004.

FIELD OF THE INVENTION

The present invention relates to a novel process for preparing cyclic ketones such as alkyl cyclopentanone-2-carboxylates. The substances obtained in this way are used as basic building blocks for pharmaceuticals and crop protection agents, as fine chemicals, for the surface coatings industry, etc.

BACKGROUND OF THE INVENTION

The intramolecular condensation reaction named after Dieckmann (Ber. Dtsch. Chem. Ges. 1894 (27) 965, Liebigs Ann. 1901 (317) 27) is known. For example, the Dieckmann condensation of dialkyl adipates leads to alkyl cyclopentanone-2-carboxylates. The process is based on a condensation reaction in which the respective alcohol is liberated:

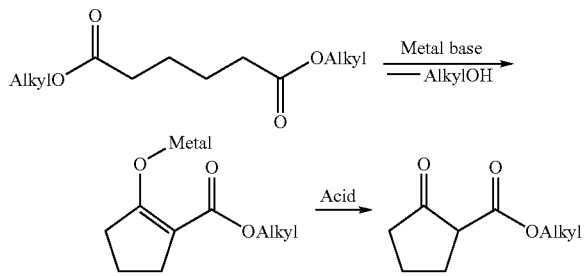

In these processes, the alkali metal salt or the alkaline earth metal salt of the desired compound is prepared with virtually quantitative conversion and selectivity and this salt is worked up under acid conditions in a further step. Many attempts to optimize the procedure and the yield of this reaction have been discussed in the literature. These relate to both the condensation agent to be used and the process methodology and solvents used.

For example, the cyclization of adipic esters by reaction with stoichiometric amounts of a strong Lewis acid (e.g. $AlCl_3$, $TiCl_2(OTf)_2$) and a base (e.g. $NEt_3$) as condensation agent has been described (e.g. Pecanha et al., Quim. Nova 20 (1997) 435; Tanabe et al., Chem. Lett. (1986) 1813). Here, the reaction takes place in solution in good yields, but stoichiometric amounts of Lewis acid and base (e.g. triethylamine) have to be used. In the subsequent aqueous work-up, the Lewis acid used is completely hydrolysed, which is undesirable from economic and ecological points of view.

In addition, many processes which bring about the cyclization by means of a strong base as condensation agent have been described. Suitable bases are, for example, alkali metals (e.g. Pinkney, Org. Synth. 1937 (17) 32), metal hydrides (e.g. Bloomfield et al., Tetrahedron Lett. 1964, 2273) or metal amides (e.g. Bouveault et al., Compt. Rend. 146 (1908) 138).

It has been found to be particularly useful to use alkoxides, in particular alkoxides of the alkali metals and alkaline earth metals, as bases (e.g. sodium ethoxide, Reed et al. J. Chem. Soc. 1954, 2148, or magnesium ethoxide, Laukkanen, Chem. Ber. 1957 (31) 124). The alkoxide is usually introduced into the reaction as a solution in the corresponding alcohol. To avoid transesterification of the starting material for the reaction or the reaction product by the alkoxide used or the alcohol used, it is usual to employ materials having an identical substitution pattern for the Dieckmann cyclization. (Methoxides in methanol for the cyclization of methyl esters, ethoxides in ethanol for the cyclization of ethyl esters, etc.). The alkoxides required are obtained either by reaction of the corresponding metal with the alcohol or by dewatering of alcoholic sodium hydroxide or potassium hydroxide.

Since Dieckmann reactions are equilibrium reactions, it is necessary to remove the alcohol liberated during the reaction and also the alcohol used as solvent quantitatively in order to achieve a quantitative conversion. A Dieckmann reaction is therefore usually carried out in nonpolar solvents such as toluene or xylene and the alcohol is distilled off.

The literature methods for Dieckmann cyclization using alkoxides in nonpolar solvents have various disadvantages for economical industrial use. A particular problem is that a viscous suspension comprising the starting materials for the reaction, the salt of the reaction product and the solvent is formed during the reaction and this can be stirred only with great difficulty from an industrial point of view. Only a low space-time yield can be achieved by means of this reaction, since it has to be carried out in a very dilute suspension which typically comprises only about 10–20% by weight of reactants and 80–90% by weight of solvent in order for the suspension to remain stirrable.

Furthermore, owing to the high viscosity of the mixture, it is usually not possible to bring about complete conversion, i.e. 100% reaction of the adipic ester, in an acceptable time. In this case, a product which still contains amounts of starting material is obtained after hydrolysis of the reaction mixture. This starting material can be separated off from the desired cyclic alkyl ketonecarboxylate by distillation only with great difficulty, since the substances have similar boiling points.

The use of various solvents which reduce the viscosity of the reaction mixture and are said to enable the Dieckmann cyclization to be carried out more easily as a result has been described.

Cassebaum et al. (DD-A 085560 (1971); Z. Chem. 1971 (11) 14) describe a process in which the reaction with sodium ethoxide as base is carried out in a solvent mixture of o-dichlorobenzene and dimethylformamide.

Richter Gedeon (HU-A 173512, 1978) likewise describe a process in which dipolar, aprotic solvents (e.g. dimethylformamide) are used for Dieckmann reactions.

Kao Corp (JP-A 9183755, 1997) carries out the reaction in solvent mixtures of aromatic organic solvents (e.g. toluene, xylene) and in tertiary alcohols (e.g. tert-butanol, amyl alcohol). The corresponding tertiary alkoxides as condensation agents are produced by reaction of the tertiary alcohol with sodium or sodium hydride.

Processes in the presence of a solvent have various disadvantages. The separation and recovery of the alcohol from the solvents used is complicated. Water present in the solvents used reacts with the strong bases used and decomposes them. Polar solvents or solvent mixtures are somewhat expensive and difficult to regenerate. They are completely or partially miscible with water, so that the polar solvent or the polar components of the solvent mixture are dissolved in the aqueous phase during the work-up of the reaction mixture as a result of acid, aqueous hydrolysis. The polar solvents can be recovered from the aqueous phase only with great difficulty. In addition, proportions of the reaction product can also be carried together with the polar solvent into the aqueous phase. When highly polar solvents or solvent mixtures are used, no phase separation occurs on hydrolysis, but instead a uniform water/solvent/product phase which can be worked up only with great difficulty is formed. The extraction with a nonpolar solvent which is necessary to recover the product from the aqueous phase and the complicated recovery of the highly polar solvent from the aqueous phase are substantial disadvantages of the methodology described.

Processes which do not use an additional solvent are therefore advantageous. VEB Fahlberg List (DE-A 2055009 (1972)) describe a process in which the reaction is carried out exclusively in the alcohol used for the synthesis of the condensation agent. For example, magnesium powder is dissolved in an excess of ethanol for the synthesis of ethyl cyclopentanone-2-carboxylate. The magnesium ethoxide formed is admixed with diethyl adipate and ethanol is distilled off, forming a resin-like mass.

This process has various disadvantages. The use of a solvent continues to be necessary. The quantitative removal of the alcohol necessary for a quantitative conversion is possible only under drastic conditions; the mixture is heated to about 220° C. for 1¾ to 2½ hours at a batch size of 1.6 mol. This procedure is unsuitable for production on an industrial scale. In the further course of the process disclosed, the resin-like mass has to be dissolved in benzene before hydrolysis. The use of additional solvents is therefore still necessary during the course of the process. Only 90% of the benzene used can be recovered.

Processes in which alcohol for dissolving the condensation agent can also be dispensed with are therefore particularly advantageous. Toda et al. (J. Chem. Soc., Perkin Trans. 1, 1998/3521) describe a method in which an alcohol for dissolving the alkoxide used is also dispensed with. Here, the dialkyl adipate is triturated with a solid alkali metal alkoxide in a pestle and mortar. The reaction product is set free from the salt by addition of p-toluenesulphonic acid. Interestingly, a quantitative conversion is not achieved in this example. A yield of 61% is reported in the reaction of diethyl adipate with sodium methoxide. A higher yield (82%) is reported when using potassium tert-butoxide as condensation agent.

This method has various disadvantages for use on an industrial scale. Costly condensation agents (e.g. sodium ethoxide) give only moderate yields. Based on the size of the batches, the specific mechanical energy introduced via the pestle is considerable.

It was therefore an object of the invention to find a technically simple process which allows the preparation of alkyl cyclopentanone-2-carboxylates with a low economic outlay while completely dispensing with solvents and at the same time resulting in complete reaction of the alkyl adipate.

SUMMARY OF THE INVENTION

This object is achieved by the process of the invention. It has surprisingly been found that complete conversion can be achieved in the absence of a solvent in a solid-state reactor or in a high-viscosity reactor.

The present invention therefore provides a process for preparing cyclic ketones of the general formula (I),

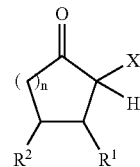

where
X is an electron-pulling group,
$R^1$ and $R^2$ are each, independently of one another, H, $C_1$–$C_{20}$-(cyclo)alkyl, $C_6$–$C_{24}$-aryl, $C_1$–$C_{20}$-(cyclo)alkyl ester or $C_1$–$C_{20}$-(cyclo)alkylamide, $C_6$–$C_{24}$-aryl ester or $C_6$–$C_{24}$-arylamide, a mixed aliphatic/aromatic radical having from 1 to 24 carbon atoms, which can also be part of a 4- to 6-membered ring, characterized in that a metal base is reacted with a compound of the general formula (II)

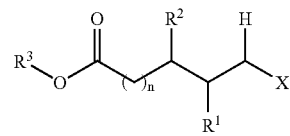

where, independently of one another, the radicals
$R^1$ and $R^2$ are as defined above,
$R^3$ is an alkyl or aryl radical and
X is an electron-pulling group, in a solid-state reactor or high-viscosity reactor without additional solvents being used.

DETAILED DESCRIPTION OF PREFERRED EMBODIMENTS

As used herein, as used in the examples or unless otherwise expressly specified, all numbers may be read as if prefaced by the word "about", even if the term does not expressly appear. Also, any numerical range recited herein is intended to include all sub-ranges subsumed therein.

The process of the invention is advantageously carried out using solid-state reactors, high-viscosity reactors or mixing kneaders which have sufficient kneading power and are provided with a facility for taking off the volatile reaction products. In addition, machines which can be evacuated and/or can additionally be heated are advantageous. The space-time yield is significantly increased by evacuation and heating and the resulting accelerated removal of the volatiles, which leads to a significant improvement in the economics. The mixing action and the input of mechanical energy in these types of apparatus are sufficient to bring about complete conversion.

The process of the invention can be carried out in single-shaft or multishaft machines. The single-shaft machines include, for example, mixing kneaders, blade dryers or comparable apparatuses which ensure homogeneous mixing of the starting materials and thus complete conversion. Examples of such apparatuses are described, for example, in EP-A 0 729 780 (Draiswerke), EP-A 0 611 937 (Draiswerke), DE-A 19 747 218 (Lödige), EP-A 0 304 925 (List).

The process of the invention is particularly advantageously carried out in multishaft mixing kneaders or high-viscosity reactors. The shafts are provided with mixing elements which can intermesh and thus ensure some self-cleaning action. The mixing or kneading shafts can be corotating or counterrotating. The rotational movement of the shafts and the kneading elements affixed thereto ensures the introduction of sufficient energy to achieve good mixing and thus complete conversion. Examples of partially self-cleaning machines may be found, for-example, in EP-A 0 329 092 (List) and EP-A 0 517 068 (List). An example of a fully self-cleaning machine is described in EPA 0 460 466 (Bayer).

The machines mentioned additionally have a large free volume which is necessary for effective removal of the volatile reaction products and thus for a good space-time yield. The apparatuses mentioned can, depending on configuration, be operated batchwise or continuously. For continuous operation, appropriate feed and discharge facilities need to be provided, as described, for example, in WO 02/20885.

The process of the invention can likewise advantageously be carried out in a multiscrew extruder. Multiscrew extruders have an extremely good mixing action and a good self-cleaning action. Corotating or counterrotating multi-screw extruders are known to those skilled in the art as machines for the reaction, plasticization and degassing of paste-like or high-viscosity media or for the transport of solids. Extruders having two or more screws are suitable. Planetary-gear extruders can also be used (e.g. DE-A 10 054 854, Entex). Frequent and effective renewal of the surface in an extruder, which ensures good mass transfer and thus rapid removal of the volatile constituents, likewise has a positive effect on the process.

In a high-viscosity reactor, maximum residence times of 30 minutes and more can be achieved, while economical residence times in an extruder are in the range from 10 seconds to 10 minutes. The way in which the process is carried out, determined by temperature and pressure, has to be matched to the circumstances of the machines. The relationship between residence time, mass transfer, temperature and pressure is known to those skilled in the art.

Any 5–7 cycloketones can be prepared by the process of the invention.

The process of the invention is suitable for producing CH-acid cycloketones of the general formula (I),

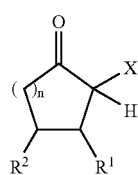

where
X is an electron-pulling group (carboxylic ester or nitrile),
$R^1$ and $R^2$ are each, independently of one another, H, $C_1$–$C_{20}$-(cyclo)alkyl, $C_6$–$C_{24}$-aryl, $C_1$–$C_{20}$-(cyclo)alkyl ester or $C_1$–$C_{20}$-(cyclo)alkylamide, $C_6$–$C_{24}$-aryl ester or $C_6$–$C_{24}$-arylamide, a mixed aliphatic/aromatic radical having from 1 to 24 carbon atoms, which can also be part of a 4- to 8-membered ring,
n is an integer from 0 to 3, with complete conversion of the parent ester component.

The electron-pulling group X can be any substituent which leads to CH acidity of the hydrogen in the a position. It can be, for example, an ester group, a nitrile group or a carbonyl group. Preference is given to ester groups, particularly preferably methyl carboxylate and ethyl carboxylate groups.

Also suitable are compounds of the general formula (I) whose ring likewise contains heteroatoms such as oxygen, sulphur or nitrogen atoms.

The activated cyclic ketone of the formula (I) preferably has a ring size of 5 (n=1) or 6 (n=2).

Preferred compounds of the general formula (I) are methyl cyclopentanone-2-carboxylate and ethyl cyclopentanone-2-carboxylate, cyclopentanone-2-carbonitrile, methyl cyclohexanone-2-carboxylate and ethyl cyclohexanone-2-carboxylate and 2-methylcarbonylcyclopentanone. Particular preference is given to methyl cyclopentanone-2-carboxylate and ethyl cyclopentanone-2-carboxylate and also methyl cyclohexanone-2-carboxylate and ethyl cyclohexanone-2-carboxylate.

The cyclopentanone systems can easily be obtained industrially by the abovementioned Dieckmann condensation of dimethyl adipate or diethyl adipate.

The invention is described by the following examples.

EXAMPLES

Preparation of Cyclic 1,3-diketo Compounds

Example 1

The process was carried out in a high-viscosity reactor model CRP 2,5 Batch from List AG. The high-viscosity reactor is a machine having two horizontal corotating mixing shafts. Kneading devices which intermesh and thus ensure rapid and homogeneous mixing are located on the shafts. In addition, the machine has a discharge screw by means of which the product can be conveyed out of the reaction chamber. It can be operated continuously or batchwise. The reactor has a free volume of about 2.5 l. The reaction chamber of the machine can be heated. Volatile constituents can be taken off via a vent. 1336 g of diethyl adipate and 472 g of sodium ethoxide were placed in the high-viscosity reactor. After start-up of the kneader and commencement of mixing of the starting materials a viscous mass was immediately formed. While kneading slowly, the temperature was slowly increased to 120° C. A vacuum of 10 mbar was slowly built up. The temperature of 120° C. was reached after about 15 minutes. Slow kneading was then continued at a temperature of 120° C. for 30 minutes until a pulverized white solid had been obtained. The powder formed was discharged by means of a transport screw and subsequently hydrolysed using half-strength sulphuric acid. Phase separation and distillation at 120° C./10 mbar gave 1021 g of ethyl cyclopentanone-2-carboxylate, viz. about 99% of theory. Diethyl adipate could no longer be detected.

Example 2

The process was carried out in a corotating twin-shaft extruder model ZSK34 having a shaft diameter of 34 mm. The process section of the machine had a length of 1560 mm. The machine was provided with an opening for the introduction of solids. The liquid was introduced via a drilled hole in the barrel. Mixing of the components is effected by the kneading elements located on the shaft. The volatile reaction products were taken off via an open venting facility. 1.31 kg/h of sodium methoxide as powder and 3.69 kg/h of diethyl adipate as liquid were metered into the machine. The rotational speed of the machine was about 60 l/min. The mixture was heated to about 150° C. by means of the barrel heating. At the end of the machine, a crumbly white solid was discharged. After acidification, aqueous work-up and extraction with an organic solvent (toluene), no starting material in the form of diethyl adipate, monomethyl adipate or adipic acid could be detected. Only ethyl cyclopentanone-2-carboxylate was found. The yield based on diethyl adipate was quantitative.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing cyclic ketones of the general formula (I),

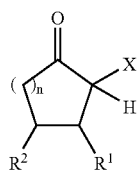
(I)

where

X is an electron-pulling group, $R^1$ and $R^2$ are each, independently of one another, H, $C_1$–$C_{20}$-(cyclo)alkyl, $C_6$–$C_{24}$-aryl, $C_1$–$C_{20}$-(cyclo)alkyl ester or $C_1$–$C_{20}$-(cyclo)alkylamide, $C_6$–$C_{24}$-aryl ester or $C_6$–$C_{24}$-arylamide, a mixed aliphatic/aromatic radical having from 1 to 24 carbon atoms, which can also be part of a 4- to 6-membered ring, wherein a metal base is reacted with a compound of the general formula (II)

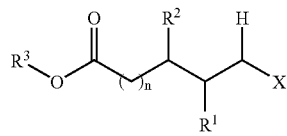
(II)

where, independently of one another, the radicals $R^1$ and $R^2$ are as defined above, $R^3$ is an alkyl or aryl radical and X is an electron-pulling group, n is an integer from 0 to 3 in a solid-state reactor or high-viscosity reactor without additional solvents being used, wherein complete conversion of starting materials is achieved.

2. Process according to claim 1, wherein the electron-pulling group X in the general formulae (I) and (II) is selected from the group consisting of ester, sulphoxide, sulphone, nitro, phosphonate, nitrile, isonitrile and carbonyl groups.

3. Process according to claim 1, wherein the electron-pulling group X in the general formulae (I) and (II) is selected from the group consisting of esters and nitrites.

4. Process according to claim 1, wherein diethyl adipate or dimethyl adipate is used as starting material.

5. Process according to claim 4, wherein metal alkoxides are used as bases.

6. Process according to claim 1, wherein a blade dryer, a single-shaft or multishaft high-viscosity reactor or a single-screw or multiscrew extruder is used as solid-state reactor.

7. Process according to claim 1, wherein the reaction and the subsequent removal of the volatile reaction products is carried out at a pressure less than or equal to atmospheric pressure and/or at a temperature greater than 20° C.

* * * * *